(12) United States Patent
Bicknell et al.

(10) Patent No.: US 9,022,989 B2
(45) Date of Patent: May 5, 2015

(54) INJECTION DEVICES

(75) Inventors: Stephen Bicknell, Warwickshire (GB); Mark Eaton, Oxon (GB)

(73) Assignee: Owen Mumford Limited, Oxford (GB)

( * ) Notice: Subject to any disclaimer, the term of this patent is extended or adjusted under 35 U.S.C. 154(b) by 549 days.

(21) Appl. No.: 12/672,914

(22) PCT Filed: Aug. 11, 2008

(86) PCT No.: PCT/GB2008/002741
§ 371 (c)(1),
(2), (4) Date: Apr. 27, 2010

(87) PCT Pub. No.: WO2009/022132
PCT Pub. Date: Feb. 19, 2009

(65) Prior Publication Data
US 2011/0196311 A1  Aug. 11, 2011

(30) Foreign Application Priority Data
Aug. 10, 2007 (GB) .................................. 0715623.5

(51) Int. Cl.
*A61M 5/00* (2006.01)
*A61M 5/32* (2006.01)
(Continued)

(52) U.S. Cl.
CPC ........... *A61M 5/2033* (2013.01); *A61M 5/3204* (2013.01); *A61M 5/326* (2013.01);
(Continued)

(58) Field of Classification Search
CPC ................ A61M 2005/202; A61M 2005/206; A61M 2005/2073; A61M 2005/3142; A61M 2005/3247; A61M 5/2033; A61M 5/3204; A61M 5/326; A61M 5/3287

USPC ......... 604/187, 181, 93.01, 48, 110, 192–198
See application file for complete search history.

(56) References Cited

U.S. PATENT DOCUMENTS 5,176,643 A  *  1/1993  Kramer et al. ................ 604/135
5,300,030 A      4/1994  Crossman et al.
(Continued)

FOREIGN PATENT DOCUMENTS

JP     H06508773 A    9/1999
JP     H11514242 A   12/1999
(Continued)

OTHER PUBLICATIONS

International search report of PCT/GB2008/002741, mailed on May 25, 2009.
(Continued)

*Primary Examiner* — Matthew F Desanto
(74) *Attorney, Agent, or Firm* — Young & Thompson

(57) ABSTRACT

An injection device has a main drive module which can be screwed into the back of a syringe housing to prepare the injector ready for use. The drive module has a firing button and a drive plunger released for forward movement by pressing the firing button. The syringe housing slideably receives a syringe holder whose forward movement is initially prevented by internally directed barbs on a cylindrical latching sleeve. The latching sleeve is acted upon by a release ring on the drive module such that as the drive module is screwed onto the syringe housing, the release ring splays the cylindrical shell to release the syringe carrier for forward movement. The barbs also act as a latch to capture the syringe carrier in its rearward position when the drive module is unscrewed from the syringe housing, which returns the barbs to their initial position before the syringe holder returns to its initial position.

7 Claims, 4 Drawing Sheets

(51) Int. Cl.
  *A61M 5/20* (2006.01)
  *A61M 5/31* (2006.01)

(52) U.S. Cl.
  CPC .. *A61M2005/206* (2013.01); *A61M 2005/2073* (2013.01); *A61M 2005/3247* (2013.01); *A61M 2005/3142* (2013.01); *A61M 2005/202* (2013.01)

(56) References Cited

U.S. PATENT DOCUMENTS

| | | | |
|---|---|---|---|
| 5,478,316 A | 12/1995 | Bitdinger et al. | |
| 5,843,036 A * | 12/1998 | Olive et al. | 604/136 |
| 5,891,086 A | 4/1999 | Weston | |
| 6,575,939 B1 * | 6/2003 | Brunel | 604/187 |
| 6,613,022 B1 * | 9/2003 | Doyle | 604/192 |
| 6,979,316 B1 * | 12/2005 | Rubin et al. | 604/156 |
| 7,101,351 B2 * | 9/2006 | Crawford et al. | 604/110 |
| 7,468,054 B2 * | 12/2008 | Crawford et al. | 604/198 |
| 7,488,308 B2 * | 2/2009 | Lesch, Jr. | 604/236 |
| 7,717,877 B2 * | 5/2010 | Lavi et al. | 604/137 |
| 7,744,561 B2 | 6/2010 | Stamp | |
| 7,901,377 B1 * | 3/2011 | Harrison et al. | 604/156 |
| 7,901,382 B2 * | 3/2011 | Daily et al. | 604/187 |
| 2003/0105430 A1 * | 6/2003 | Lavi et al. | 604/136 |
| 2005/0027255 A1 * | 2/2005 | Lavi et al. | 604/135 |
| 2006/0069350 A1 | 3/2006 | Buenger et al. | |
| 2006/0276756 A1 | 12/2006 | Francavilla | |
| 2007/0265568 A1 * | 11/2007 | Tsals et al. | 604/136 |
| 2007/0270759 A1 | 11/2007 | Pessin | |

FOREIGN PATENT DOCUMENTS

| | | |
|---|---|---|
| JP | 2006515998 A | 6/2006 |
| JP | 2006516461 A | 7/2006 |
| WO | 9910030 A2 | 3/1999 |
| WO | 03045481 A1 | 6/2003 |
| WO | 2004069302 | 8/2004 |
| WO | 2005115513 A1 | 12/2005 |
| WO | 2006027447 | 3/2006 |
| WO | 2007027204 A2 | 3/2007 |

OTHER PUBLICATIONS

GB Search Report, dated Oct. 29, 2007, from corresponding GB application.

* cited by examiner

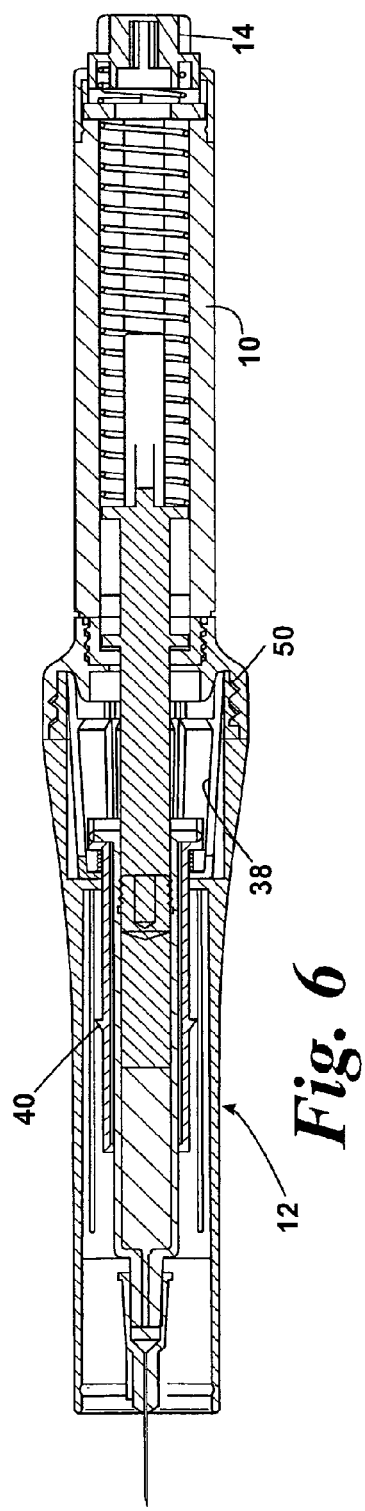
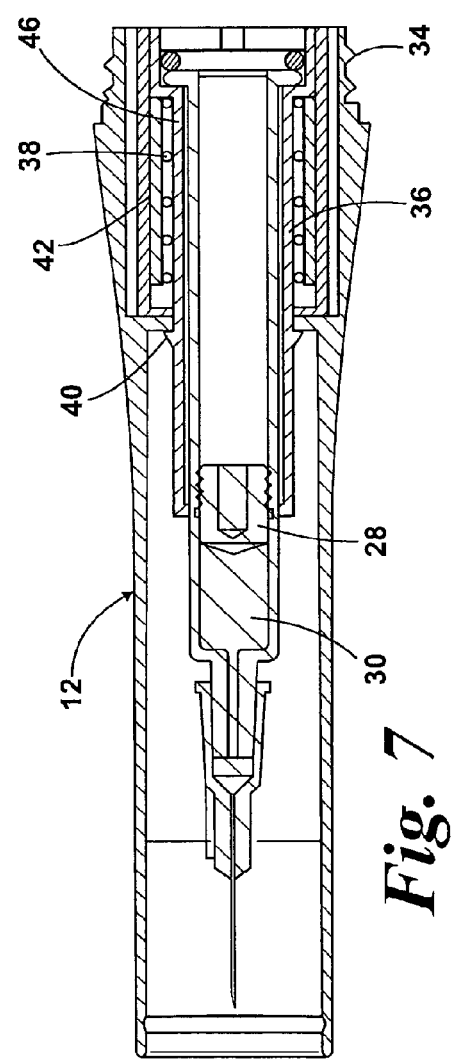
Fig. 6
Fig. 7

INJECTION DEVICES

This invention relates to injection devices and in particular, but not exclusively, to automatic injector devices having a mechanism which moves a syringe within the device forwardly so that the needle tip projects from the device and then delivers the dose through the needle.

Many automatic injectors are designed to deliver one dose and then to be discarded after use. Although often the cost of the drug dispensed is much greater than the cost of the injector device, there is a concern to reduce the cost of the drug delivery system and also an environmental desire to reuse components where necessary. We have therefore designed an automatic injector device in which the drive mechanism may be reused and provided as a separate module which is screwed or otherwise coupled to a housing containing the syringe, so that the driver module can be reused many times. However the design of such a device means that internal access to the forward portion is possible and so it is desirable to provide some means of preventing movement of the syringe in the housing when separate from the drive module, so as to prevent the possibility of a syringe being pushed forwardly in the housing to expose the needle either before or after use. In other, manually operated devices, it is also desirable to disable or make safe an injection device before and after use.

Accordingly, in one aspect, this invention provides an injection device comprising:
- a main housing portion;
- a syringe having a needle, said syringe being mounted in said housing portion for movement between a rearward position in which said needle is shrouded by a forward part of said housing portion, and a forward position in which said needle projects forwardly of said housing for delivery of a dose;
- locking means for locking said syringe in a rearward position, said locking means being releasable to allow forward movement of the syringe, and
- latch means operable to latch the released syringe in a rearward position after delivery of a dose.

The syringe is conveniently held in a syringe holder that cooperates with said locking means and said latching means.

Preferably said locking means and said latching means are defined by a common moveable locking/latching element moveable between:
- a locking/latching position in which it (i) prevents movement of said syringe forwardly from a rearward position, and (ii) latches said syringe against forward movement when returning from a forward position towards a rearward position,
and
- an unlocked position in which the syringe is allowed to move forward.

The latching/locking element may comprise at least one latch portion moveable generally transversely relative to the syringe between said locking/latching position and said unlocked position. Each latch portion may be carried on a respective finger moveable transversely between said locking/latching position and said unlocked position. Thus a plurality of latching portions may be provided on arcuate wall portions of a generally cylindrical resiliently expandable locking sleeve.

Said locking sleeve is preferably releasable by axial engagement and shifting of said wall portions by a release ring portion.

Where the device includes a driver mechanism disposed in a drive housing having a forward end for releasable engagement with the rear end of said housing portion, said locking means and said latching means may be designed to be released upon a predetermined extent of engagement between said drive housing and said main housing portion.

Where said main housing portion and said drive housing portion are threadedly engageable said drive portion may carry a release ring portion for engaging said locking sleeve.

Whilst the invention has been described above, it extends to any inventive combination of the features set out above, or in the following description.

The invention may be performed in various ways, and an embodiment thereof will be described by way of example only, reference being made to the accompanying drawings in which.

Figure 5A:
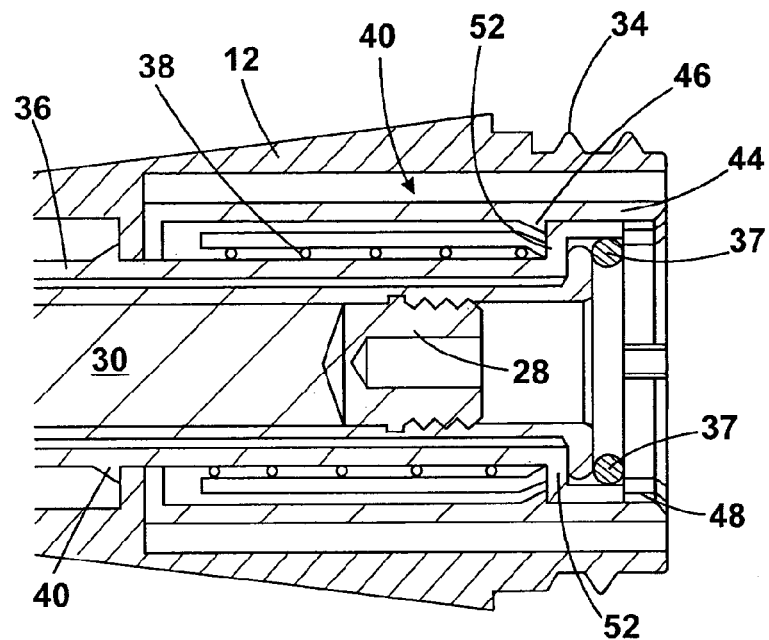
Figure 5B:
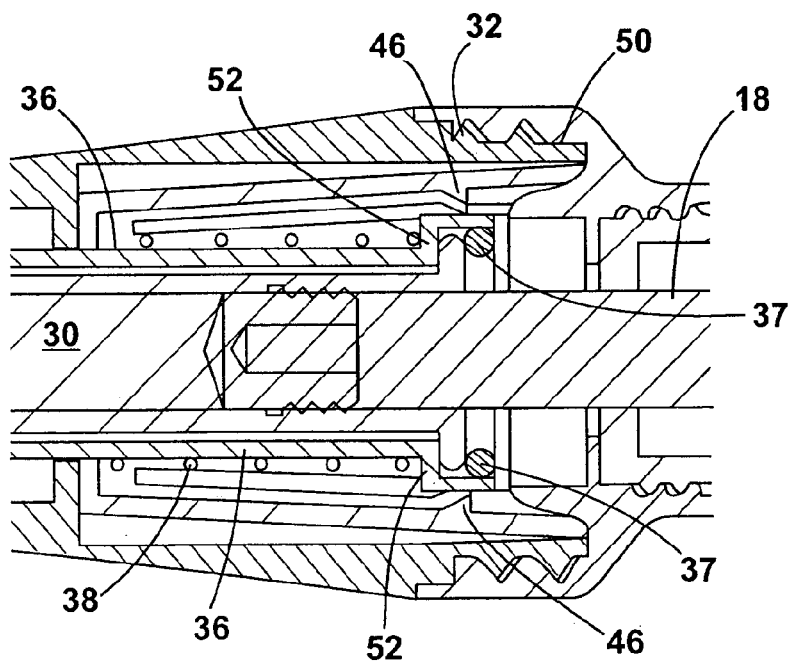

FIGS. 5(*a*) and (*b*) are enlarged views showing the latch sleeve in its latching position and its open position respectively.

Figure 1:
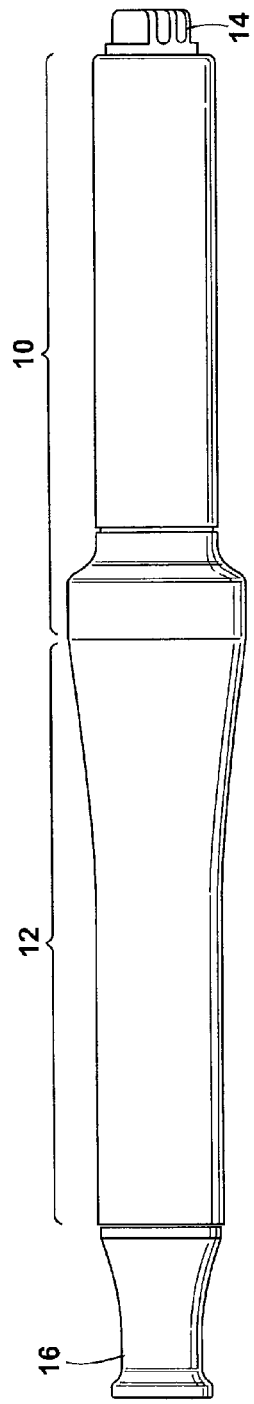
FIG. 1 is a side view of an automatic injector with a separate drive module screwed onto the rear end of a forward housing containing the syringe.

FIG. 6 is a view similar to FIG. 1 but showing the device when fired, and FIG. 7 is a section view showing the forward portion unscrewed from the drive module after use.

Referring to the drawings, the embodiment of injection device disclosed therein is an automatic injector comprising a drive module 10 which can be screwed into the back of a syringe housing 12 to prepare the injector ready for use. The device has a firing button 14 at its rear end and the front end of the syringe housing is initially covered by a cap 16. The drive module 10 slideably supports a drive plunger 18 which is urged forwardly by means of a drive spring 20. At the rear end, the plunger 18 is formed with a split arrowhead configuration 22 which enables the plunger to latch in a cocked position behind an internal wall in the module casing.

In order to fire the device, the firing button 14 is rotated from a safe to an armed position and then pushed forwardly so as to squeeze the arrowheads together releasing the plunger for forward movement under the influence of the drive spring 20. Forward movement of the plunger is limited by an annular rib 26 which co-operates with an end wall in the drive housing 10. The forward end of the drive plunger 18 is of reduced diameter to fit within a bung 28 of the syringe 30. At its front end, drive module 10 has a female threaded portion 32 threadable onto a corresponding male threaded portion 34 on the rear of the syringe housing 12.

Figure 2:
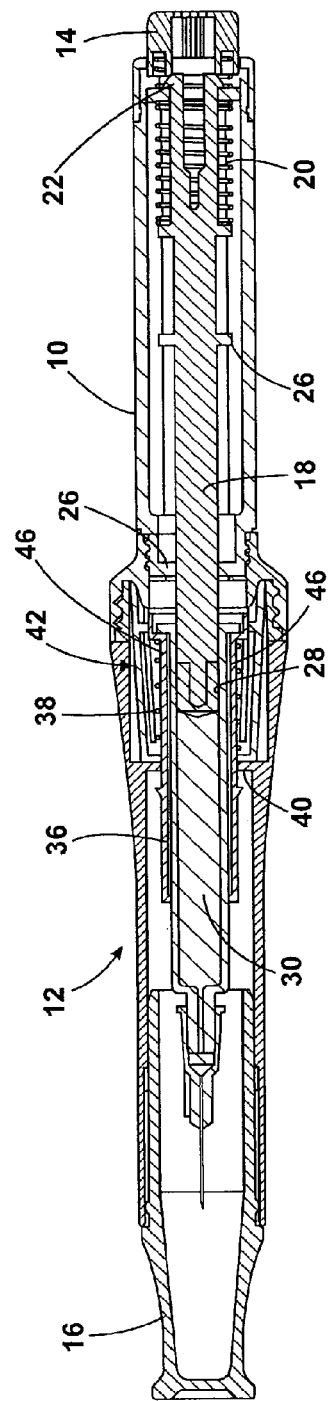
FIG. 2 is a longitudinal sectional view taken on lines: II-II of FIG. 1.

The syringe housing 12 slideably receives a syringe holder 36 mounted for slideable movement within the housing 12, urged rearwardly by a compression spring 38, the rearward movement being constrained by a shoulder on a snap fit annulus 40 on the syringe holder. The syringe 30 is concentrically held within the syringe holder 36 by snap detent features 37, that clip behind the skirt at the rear end of the syringe, and moves axially therewith between the rearward position shown in FIG. 2 and the forward position shown in FIG. 6.

Figure 3:
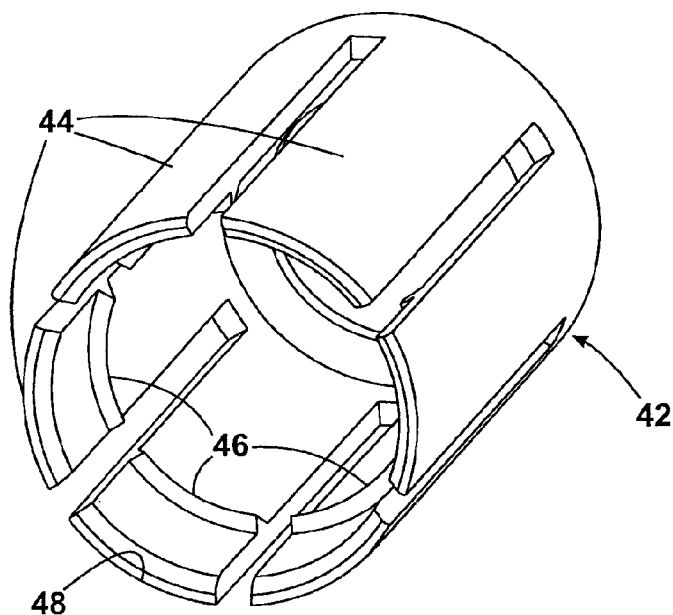
FIG. 3 is a detailed view on the latching sleeve.
Figure 4:
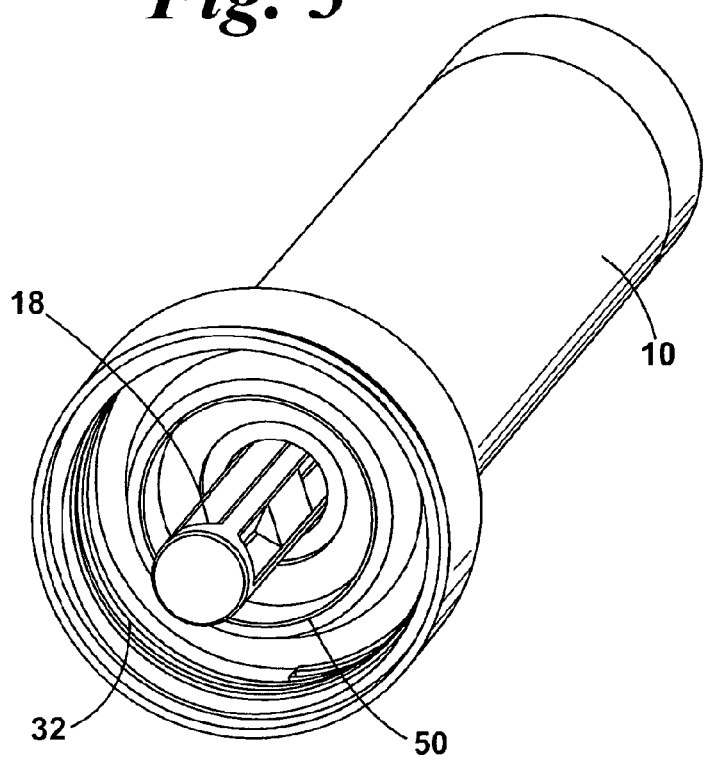
FIG. 4 is an isometric view looking rearwardly on the drive module.

Concentrically surrounding the syringe holder 36 and the spring 38 is a cylindrical latching shell 42 whose form can be seen more clearly in FIG. 3. The latching shell 42 has slots dividing its cylindrical surface into six arcuate resiliently deformable arms 44, each having an internally directed barb 46 short of the end thereof. The free ends of the resilient arms 44 are chamfered as shown at 48.

The latching sleeve 42 is acted on by a release ring portion 50 on the front end of the drive module so that, as the drive module is screwed into the back of the syringe housing, the release ring portion 50 engages the chamfered portions 48 to splay out the resilient arms 44 to lift them from the locking position, shown in FIG. 5 where they abut and block the path of movement of a shoulder 52 on the syringe holder 36, to the splayed position shown in FIG. 5, where the arms are deflected outwardly so that the barbs 46 are clear of the path of movement of the syringe holder 36.

The co-operation of the release ring portion 50 and the latching sleeve 42 means that, when the syringe housing 12 is separated from a drive module 10, the sleeve is in its relaxed position in which the barbs 46 block movement of the syringe carrier 36. Also, after use, when the drive module 10 has been unscrewed from the syringe housing the barbs again return to their locking position to latch and prevent forward movement of the used syringe as it returns to its rear position.

The cap 16 may have inwardly directed fingers or a suitable engagement surface (not shown) which grips a sheath (not shown) initially covering the syringe needle, or otherwise engages the sheath so that removal of the cap from the device also pulls the sheath off the needle.

In use, the drive module is cocked and the cap is removed from the front end of a syringe housing. The drive module is then screwed into the back of the syringe housing. Towards the end of the threaded engagement the release ring portion 50 engages the chamfers 48 thus splaying the arms of the latching sleeve to release the syringe holder 36 for movement.

The device is then offered up to the user's skin. The button 14 is turned to the armed position and pressed to release the plunger. The plunger shoots forward driving the syringe 30 forwardly with it due to the incompressible nature of the syringe contents so that the needle projects beyond the forward end of the housing. The syringe is arrested and the spring 38 is fully compressed and thereafter the plunger drives the bung 28 forwardly to expel the dose. At this stage the components are in the configuration shown in FIG. 6.

The user then unscrews the drive module 10 from the syringe housing 12 and the release ring 50 is drawn out of engagement with the latching sleeve so that it returns to the position shown in FIG. 5. The syringe carrier is urged rearwardly by the spring 38 as the drive module is unscrewed and, when the parts separate and the drive module 10 is pulled away from the forward housing, the syringe carrier snaps past the barbs 46 so that it is locked in its rearward position.

The invention claimed is:

1. An injection device comprising:
   a forward housing;
   a drive housing having a forward end configured to be attached to and detached from a rear end of said forward housing, the drive housing including a drive mechanism;
   a syringe having a needle, said syringe being mounted in said forward housing for movement between a rearward position in which said needle is shrouded by a forward part of said forward housing, and a forward position in which said needle projects forwardly of said forward housing for delivery of a dose;
   a locking/latching arrangement moveable between:
   (a) a locking/latching position in which said locking/latching arrangement:
      (i) prevents movement of said syringe forwardly from a rearward position, and
      (ii) latches said syringe as it returns from a forward position to a rearward position, and
   (b) an unlocked position in which the syringe is allowed to move forward,
   the locking/latching arrangement being configured to be responsive to attachment and detachment of said drive housing and said forward housing wherein:
   when the forward housing and the drive housing are detached, the locking/locking arrangement is in said locking/latching position,
   upon attaching said drive housing to said forward housing, when a predetermined extent of engagement between said drive housing and said forward housing is reached or exceeded, said locking/latching arrangement is released and said locking/latching arrangement is moved to its unlocked position, and
   upon detaching said drive housing and said forward housing, when a predetermined extent of disengagement between said drive housing and said forward housing is reached or exceeded, said latching arrangement returns to its locking/latching position.

2. An injection device according to claim 1, wherein said locking/latching arrangement comprises at least one latch portion moveable generally transversely relative to the syringe between said locking/latching position and said unlocked position.

3. An injection device according to claim 2, wherein each latch portion is carried on a respective finger moveable transversely between said locking/latching position and said unlocked position.

4. An injection device according to claim 3, wherein a plurality of latching portions are provided on arcuate wall portions of a generally cylindrical resiliently expandable locking sleeve.

5. An injection device according to claim 4, wherein said locking sleeve is releasable by axial engagement and shifting of said wall portions by a release ring portion.

6. An injection device according to claim 5, wherein said forward housing and said drive housing are threadedly engageable and said drive housing carries a release ring portion for engaging said locking sleeve.

7. An injection device according to claim 1, wherein said syringe is held in a syringe holder and said locking/latching arrangement cooperates with said syringe holder.

* * * * *